United States Patent
Davis, Jr. et al.

(10) Patent No.: US 9,463,951 B1
(45) Date of Patent: Oct. 11, 2016

(54) GAS SUPPLY SYSTEM

(71) Applicants: Thomas Oliver Davis, Jr., Orient, OH (US); Nancy Sue Davis, Orient, OH (US)

(72) Inventors: Thomas Oliver Davis, Jr., Orient, OH (US); Nancy Sue Davis, Orient, OH (US)

( * ) Notice: Subject to any disclaimer, the term of this patent is extended or adjusted under 35 U.S.C. 154(b) by 282 days.

(21) Appl. No.: 14/325,271

(22) Filed: Jul. 7, 2014

Related U.S. Application Data

(60) Provisional application No. 61/843,323, filed on Jul. 5, 2013.

(51) Int. Cl.
*B65H 75/34* (2006.01)
*A61M 16/00* (2006.01)

(52) U.S. Cl.
CPC .......... *B65H 75/34* (2013.01); *A61M 16/0003* (2014.02)

(58) Field of Classification Search
USPC .............. 137/355.12, 355.16, 355.17, 355.2, 137/355.21; 128/205.24, 204.18, 207.16
See application file for complete search history.

(56) References Cited

U.S. PATENT DOCUMENTS

| | | | |
|---|---|---|---|
| 794,399 A | 7/1905 | Erxleben | |
| 1,045,069 A | 11/1912 | Nuhring | |
| 1,077,146 A | 10/1913 | Lemon | |
| 1,502,518 A | 7/1924 | Nasta | |
| 1,675,140 A | * 6/1928 | Schenderlein | ......... B65H 75/38 137/355.23 |
| 1,683,911 A | 9/1928 | Morris | |
| 1,746,995 A | 2/1930 | Edwards | |
| 2,301,208 A | * 11/1942 | Gear | .................. B65H 75/4407 137/355.2 |
| 2,596,766 A | 5/1952 | Dugdale | |
| 2,629,630 A | * 2/1953 | Roark | .................... B65H 75/38 137/355.17 |
| 2,711,734 A | 6/1955 | Moe | |
| 2,904,272 A | 9/1959 | Barrett | |
| 3,184,180 A | 5/1965 | Rockwell | |
| 3,437,105 A | 4/1969 | Stracek | |
| 4,757,838 A | 7/1988 | McGullion | |
| 5,390,695 A | 2/1995 | Howard | |
| 5,392,808 A | 2/1995 | Pierce | |

(Continued)

FOREIGN PATENT DOCUMENTS

EP 2116270 A1 11/2009

OTHER PUBLICATIONS

First office action on the merits (Non-Final Rejection) in U.S. Appl. No. 12/115,842, dated Apr. 29, 2011.

(Continued)

*Primary Examiner* — Craig Schneider
*Assistant Examiner* — Daniel P Donegan
(74) *Attorney, Agent, or Firm* — The Law Office of Patrick F. O'Reilly III, LLC

(57) ABSTRACT

A gas supply system includes a housing with an aperture, a spool, a one-way bearing, an interval locking device, a main keyed shaft, a spring housing, a spring torque spool and a pair of spring grounding tabs, a main base that stabilizes the housing, a rotating shaft where the main base is disposed on the distal end of the rotating shaft, a rotational bearing that is disposed on the proximal end of the rotating shaft and connects the rotating shaft to the main base. There is also a base clamp that has a pair of corresponding apertures and secures the gas supply system to a tubular shaped object and an adjustable clamp screw that has a handle and a threaded bolt wherein the proximal end of the threaded bolt is attached to and perpendicularly extends from the handle and the adjustable clamp screw.

11 Claims, 7 Drawing Sheets

(56) References Cited

U.S. PATENT DOCUMENTS

| | | |
|---|---|---|
| 5,787,923 A | 8/1998 | Shea et al. |
| 5,826,608 A | 10/1998 | Pierce |
| 5,975,120 A | 11/1999 | Novosel |
| 6,065,490 A | 5/2000 | Falcone, Jr. |
| 6,095,922 A | 8/2000 | Friedrichsen et al. |
| 6,478,265 B2 | 11/2002 | Leach |
| 6,588,444 B2 | 7/2003 | Paplow et al. |
| 6,591,858 B2 | 7/2003 | Peterson |
| 6,889,688 B1 | 5/2005 | Wright |
| 6,978,960 B2 | 12/2005 | Schaller |
| 7,104,491 B2 | 9/2006 | Vinding |
| 7,216,665 B1 | 5/2007 | Sims, Jr. |
| 7,857,000 B1 | 12/2010 | Langdon |
| 8,578,960 B2 | 11/2013 | Davis, Jr. |
| 2002/0195143 A1* | 12/2002 | Paplow .................. B65H 75/40 137/355.2 |
| 2003/0146332 A1 | 8/2003 | Vinding |
| 2005/0178440 A1 | 8/2005 | Huang |
| 2009/0277454 A1 | 11/2009 | Davis et al. |
| 2012/0168002 A1 | 7/2012 | Davis |

OTHER PUBLICATIONS

Second office action on the merits (Final Rejection) in U.S. Appl. No. 12/115,842, dated Sep. 2, 2011.

First office action on the merits (Non-Final Rejection) in U.S. Appl. No. 13/409,617, dated Aug. 2, 2012.

Notice of Allowance in U.S. Appl. No. 13/409,617, mailed on Apr. 5, 2013.

Supplemental Notice of Allowance in U.S. Appl. No. 13/409,617, mailed on Jul. 16, 2013.

European Search Report for European Patent Appl. No. EP 09 25 1055.1, dated Jul. 10, 2009.

European Written Opinion for European Patent Appl. No. EP 09 25 1055.1, dated Aug. 4, 2009.

First office action for European Patent Appl. No. EP 09 25 1055.1, dated Jul. 8, 2010.

Second office action for European Patent Appl. No. EP 09 25 1055.1, dated Jul. 18, 2011.

\* cited by examiner

GAS SUPPLY SYSTEM

CROSS-REFERENCE TO RELATED APPLICATIONS

This patent application claims priority to, and incorporates by reference in its entirety, U.S. Provisional Patent Application No. 61/843,323, entitled "Gas Supply System", filed on Jul. 5, 2013.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The present invention relates generally to delivery of therapeutic gases such as oxygen, nitrous oxide and the like to patients, and, more particularly, to a gas supply system capable of delivering a gas or a therapeutic gas from a gas supply to a nasal cannula connected to a patient's nose.

2. Background

During surgeries and other medical treatments, patients often require a supply of therapeutic gases, for example, oxygen, nitrous oxide, and the like. A source of the therapeutic gases may include an air canister gas supply system, an air supply cylinder, and the like. The therapeutic gases may be supplied to the patient from the source using a gas tube and a nasal cannula. More specifically, one end of the gas tube is connected to the source and the other end to the nasal cannula. Further, the nasal cannula is used to administer the therapeutic gases into the patient through their nose.

Moreover, when the gas tube is dragged along a dirty floor of the room due to the patient's movement, the gas tube may get soiled. Accordingly, the patient using such a soiled gas tube may catch infection. Further, the gas tube lying on the floor or dragged along the room may affect aesthetic appeal of the room and may provide an unorganized environment to the patient.

Accordingly, based on the foregoing, there is a need for a gas supply system that allows a patient to move freely and conveniently inside a room while being administered a therapeutic gas from the gas supply system. Moreover, the gas supply system should prevent a gas tube from lying on a floor of the room and being dragged along the floor. Further, there is a need for a gas supply system that keeps a gas tube clean, thereby reducing chances of causing infection to a patient. Furthermore, there is a need for a gas supply system that enables a user to preserve the aesthetics of the room, thereby providing an organized environment to the patient.

BRIEF SUMMARY OF EMBODIMENTS OF THE INVENTION

Accordingly, the present invention is directed to a gas supply system that substantially obviates one or more problems resulting from the limitations and deficiencies of the related art.

Accordingly, an object of one or more embodiments of the present invention is to provide a gas supply system that allows a patient to move freely and conveniently inside a room while being administered a therapeutic gas from the gas supply system.

Another object of one or more embodiments of the present invention is to provide a gas supply system that prevents a gas tube from lying on a floor of the room and being dragged along the floor.

Yet another object of one or more embodiments of the present invention is to provide a gas supply system that keeps a gas tube clean, thereby reducing chances of causing infection to a patient.

In light of the above objects, in one aspect of the present invention, a gas supply system is disclosed. The gas supply system is capable of delivering gas from a gas supply to a nasal cannula and capable of being removably mounted on a supporting member.

In accordance with one or more embodiments of the present invention, there is provided a gas supply system, comprising: a housing that includes an aperture, a spool, a one way bearing circumscribing a vertically-oriented small shaft, an interval locking device, a vertically-oriented keyed shaft, a spring housing, and a spring torque spool configured to secure a free end of a spring; a main base that stabilizes the housing in an upright perpendicular position; a vertically-oriented rotating shaft that has a proximal end and a distal end where the main base is disposed on the distal end of the vertically-oriented rotating shaft; a base clamp having opposed upper and lower offset portions, the upper offset portion having a top surface, the base clamp further including a pair of corresponding apertures, the base clamp configured to secure the gas supply system to a tubular shaped object; a rotational bearing that is disposed on the top surface of the base clamp and at the proximal end of the vertically-oriented rotating shaft, the rotational bearing connecting the vertically-oriented rotating shaft to the base clamp; and an adjustable clamp screw that has a handle and a threaded bolt with a proximal end and a distal end wherein the proximal end of the threaded bolt is attached to and perpendicularly extends from the handle of the adjustable clamp screw.

In a further embodiment of the present invention, the housing is generally cylindrical in shape.

In yet a further embodiment, the base clamp is configured to support padding disposed thereon, the padding configured to prevent damage to the base clamp or the tubular shaped object.

In still a further embodiment, the adjustable clamp screw is rotated and screwed through the pair of corresponding apertures of the base clamp to tighten the base clamp around the tubular or other suitably shaped object.

In yet a further embodiment, the spool has a top inverted frusto-conical portion and a bottom frusto-conical portion, the top inverted frusto-conical portion being disposed at a higher elevation than the bottom frusto-conical portion relative to a horizontal reference plane beneath the gas supply system, the spool being configured to receive and wind oxygen gas tubing within the housing from the aperture.

In still a further embodiment, the interval locking device is disposed between an upper portion of the spring housing and the one way bearing, the interval locking device configured to lock the oxygen gas tubing at a plurality of locations or intervals along the rotation of the spool.

In yet a further embodiment, the spring housing is placed on the vertically-oriented keyed shaft underneath the interval locking device such that the spring housing is disposed at a lower elevation than the interval locking device relative to a horizontal reference plane beneath the gas supply system, the spring housing configured to house the spring.

In still a further embodiment, the vertically-oriented keyed shaft includes one or more elongated protruding portions extending radially outward from a circumferential surface thereof.

In yet a further embodiment, the spring torque spool rotates with the keyed shaft and is disposed at a bottom of the vertically-oriented keyed shaft.

In still a further embodiment, the gas supply system includes a sleeve disposed underneath the main base such that the sleeve is disposed at a lower elevation than the main base relative to a horizontal reference plane beneath the gas supply system, the sleeve being attached to the distal end of the vertically-oriented rotating shaft by a pin.

In yet a further embodiment, the gas supply system includes a receiving nut at the distal end of the threaded bolt.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL
VIEWS OF THE DRAWINGS

The invention will now be described, by way of example, with reference to the accompanying drawings, in which.

Figure 4:
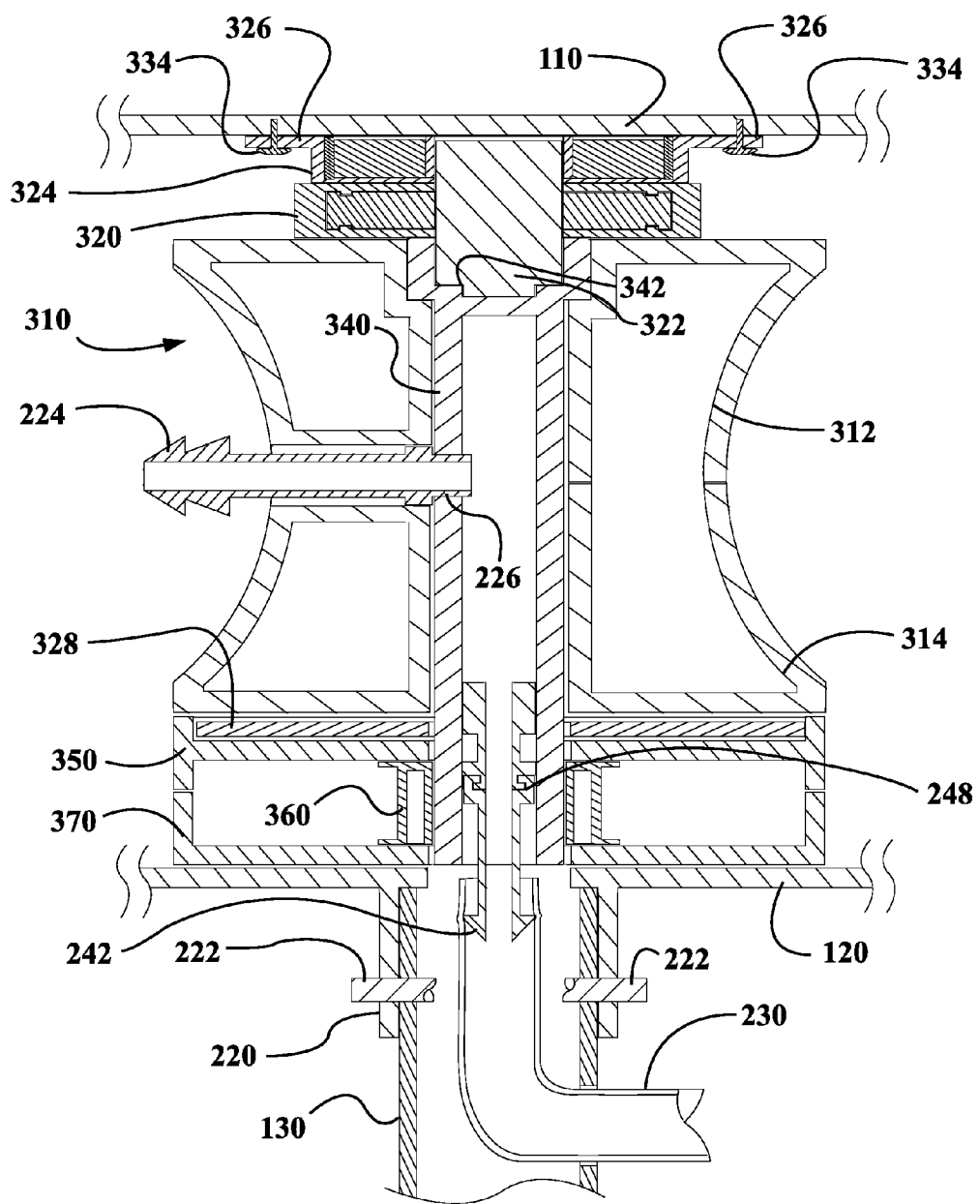
FIG. 4 illustrates a sectional view of a gas supply system, wherein the section is cut along cutting plane line A-A in FIG. 1, in accordance with the first embodiment of the present invention.
Figure 5:
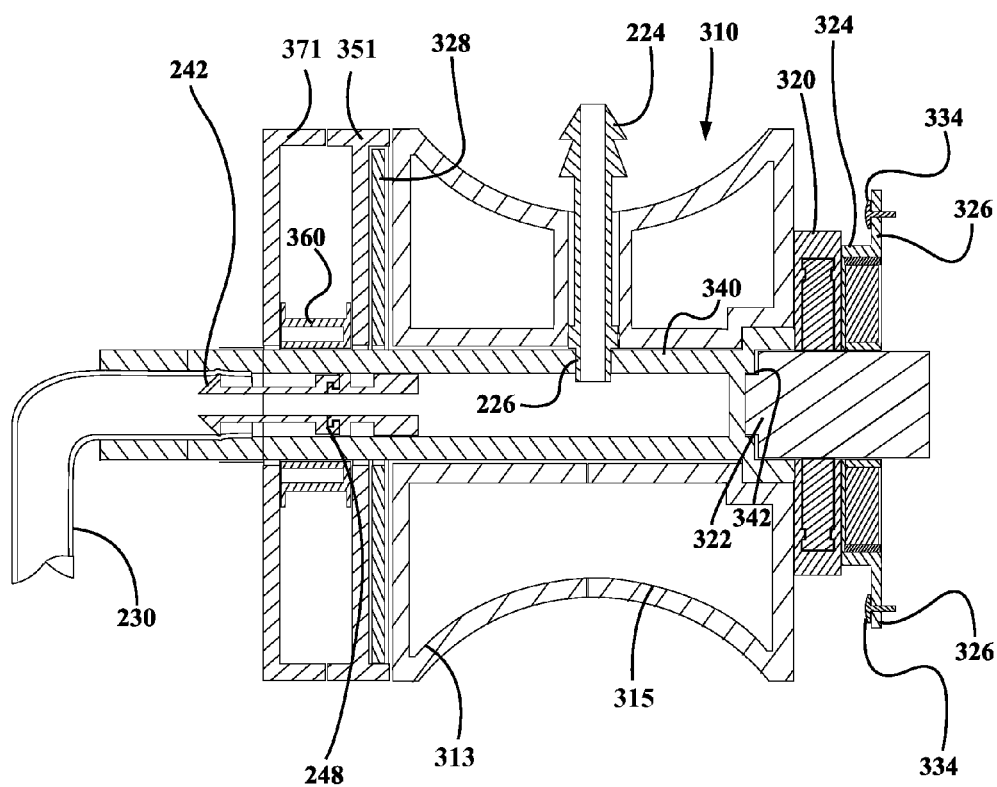
Figure 6:
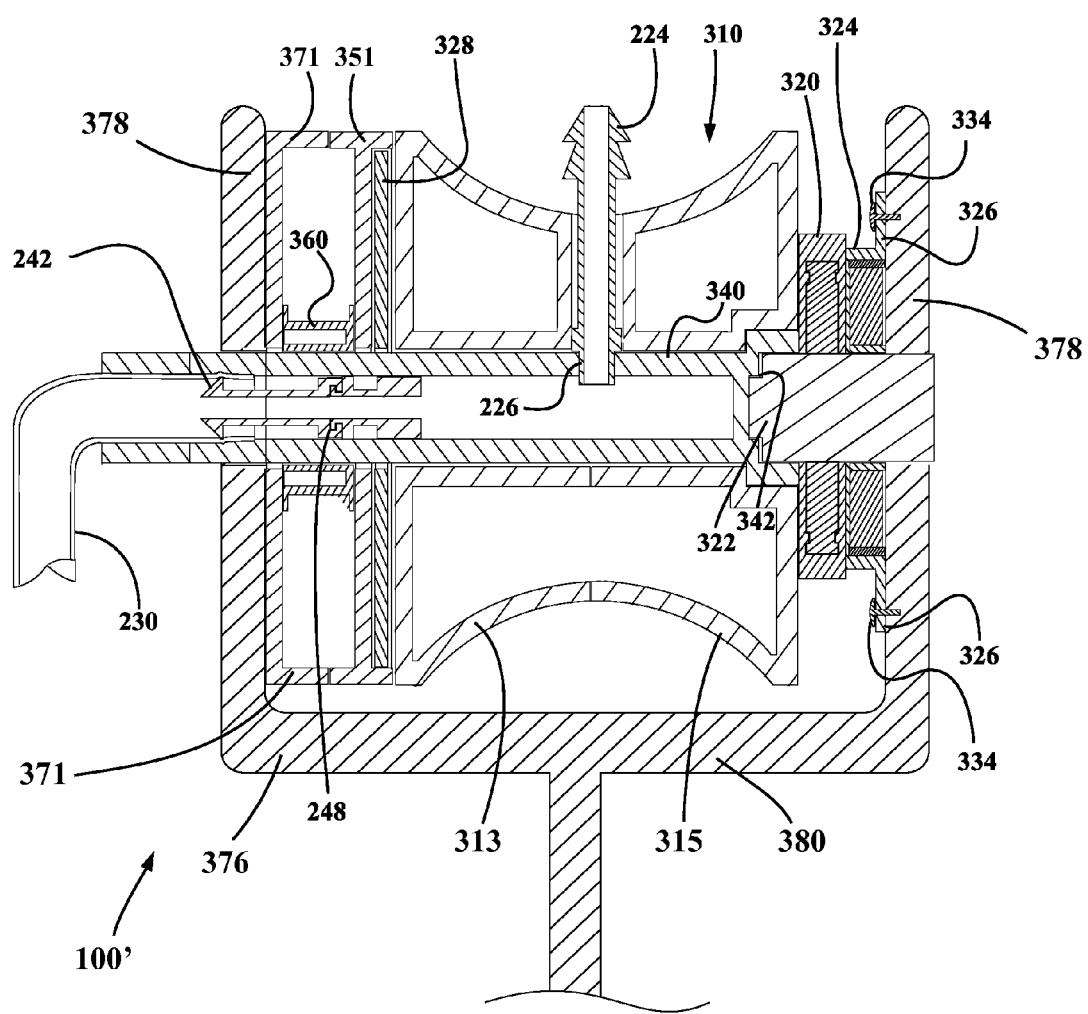

FIG. 5 illustrates a sectional view of a gas supply system, in accordance with a second embodiment of the present invention, wherein the sectional view is similar to that of FIG. 4, except that the spool of the gas supply system rotates about a horizontal axis, rather than a vertical axis; and FIG. 6 illustrates another sectional view of a gas supply system, in accordance with the second embodiment of the present invention, wherein the support yoke member of the gas supply system is shown together with the rest of the constituent system components.

Throughout the figures, the same parts are always denoted using the same reference characters so that, as a general rule, they will only be described once.

DETAILED DESCRIPTION OF EMBODIMENTS
OF THE INVENTION

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
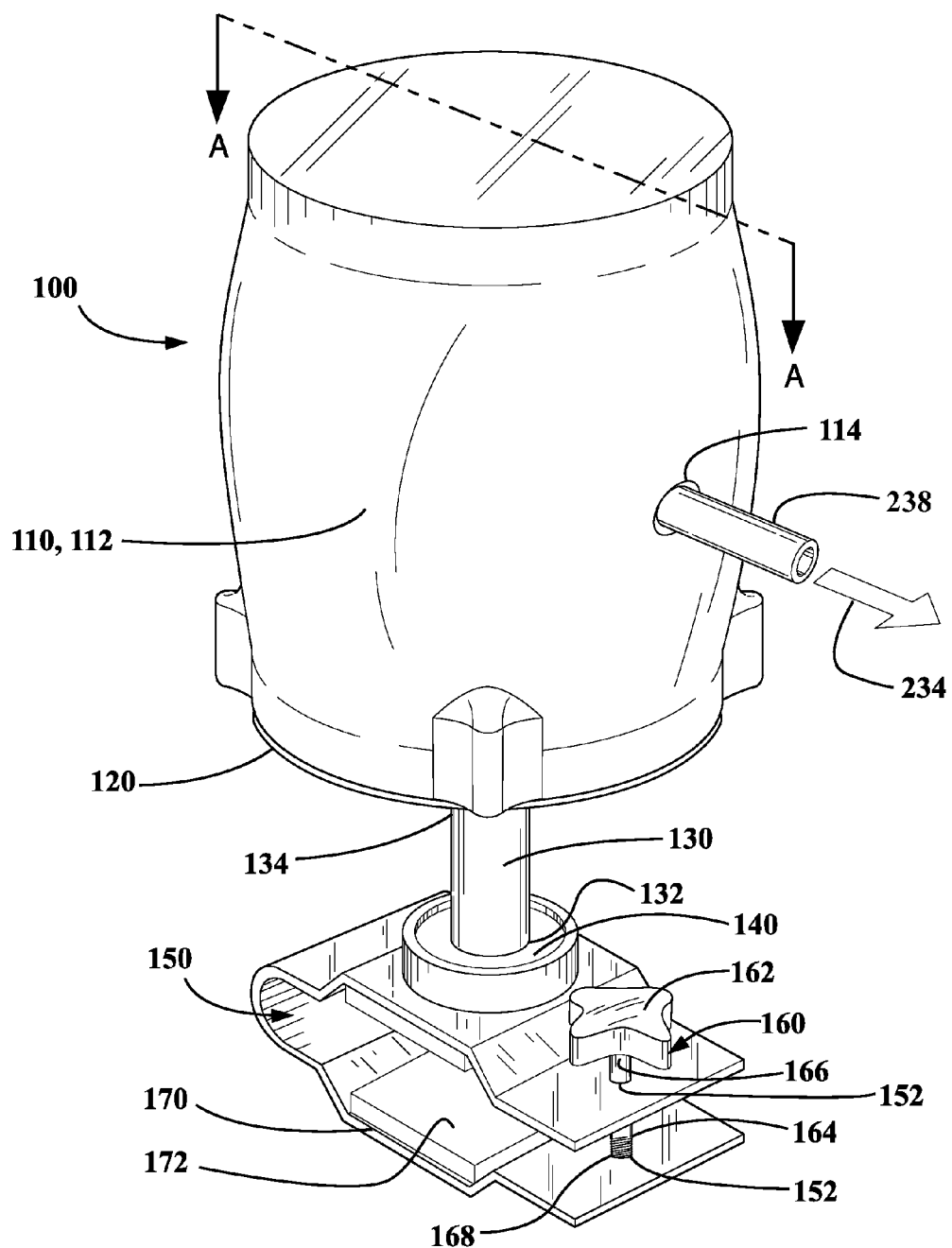
FIG. 1 illustrates a diagonal perspective view of a gas supply system, in accordance with a first embodiment of the present invention, wherein the spool of the gas supply system rotates about a vertical axis.

FIG. 1 illustrates a gas supply system 100, in accordance with a first embodiment of the present invention. The gas supply system 100 typically contains oxygen but can contain any suitable medical related gas. In the first embodiment, the tubing spool 310 (see FIGS. 3 and 4) rotates about a vertical axis.

The gas supply system 100 includes a housing 110, a main base 120, a rotating shaft 130, a rotational bearing 140, a base clamp 150 and an adjustable clamp screw 160. The housing 110 houses a plurality of gas supply canister components described and illustrated in FIGS. 3 and 4. The housing 110 is generally cylindrical-shaped 112 but can be any suitable housing shape. The housing 110 also includes an aperture 114 for allowing the passage of outlet oxygen tubing 238 therethrough (arrow 234 indicates the direction of oxygen flow). The main base 120 stabilizes the housing 110 in an upright perpendicular position. The rotating shaft 130 has a proximal end 132 and a distal end 134 where the main base 120 is disposed on the distal end 134 of the rotating shaft 130. The rotational bearing 140 is disposed on the proximal end 132 of the rotating shaft 130 and connects the rotating shaft 130 to the base clamp 150. The base clamp 150 has a pair of corresponding apertures 152 and secures the gas supply system 100 to a tubular or other suitably shaped object (not shown) such as a bed post or bed frame. The base clamp 150 has foam or other suitable padding 172 between the base clamp 150 and the tubular or other suitably shaped object. The padding 172 is disposed on a clamp surface 170 of the base clamp 150 to prevent damage to the base clamp 150 or the tubular or other suitably shaped object. The adjustable clamp screw 160 has a handle 162 and a threaded bolt 164 with a proximal end 166 and a distal end 168. The proximal end 166 of the threaded bolt 164 is attached to and perpendicularly extends from the handle 162. The adjustable clamp screw 160 is rotated and screwed through the pair of corresponding apertures 152 of the base clamp 150 to tighten the base clamp 150 around the tubular or other suitably shaped object.

Figure 2A:
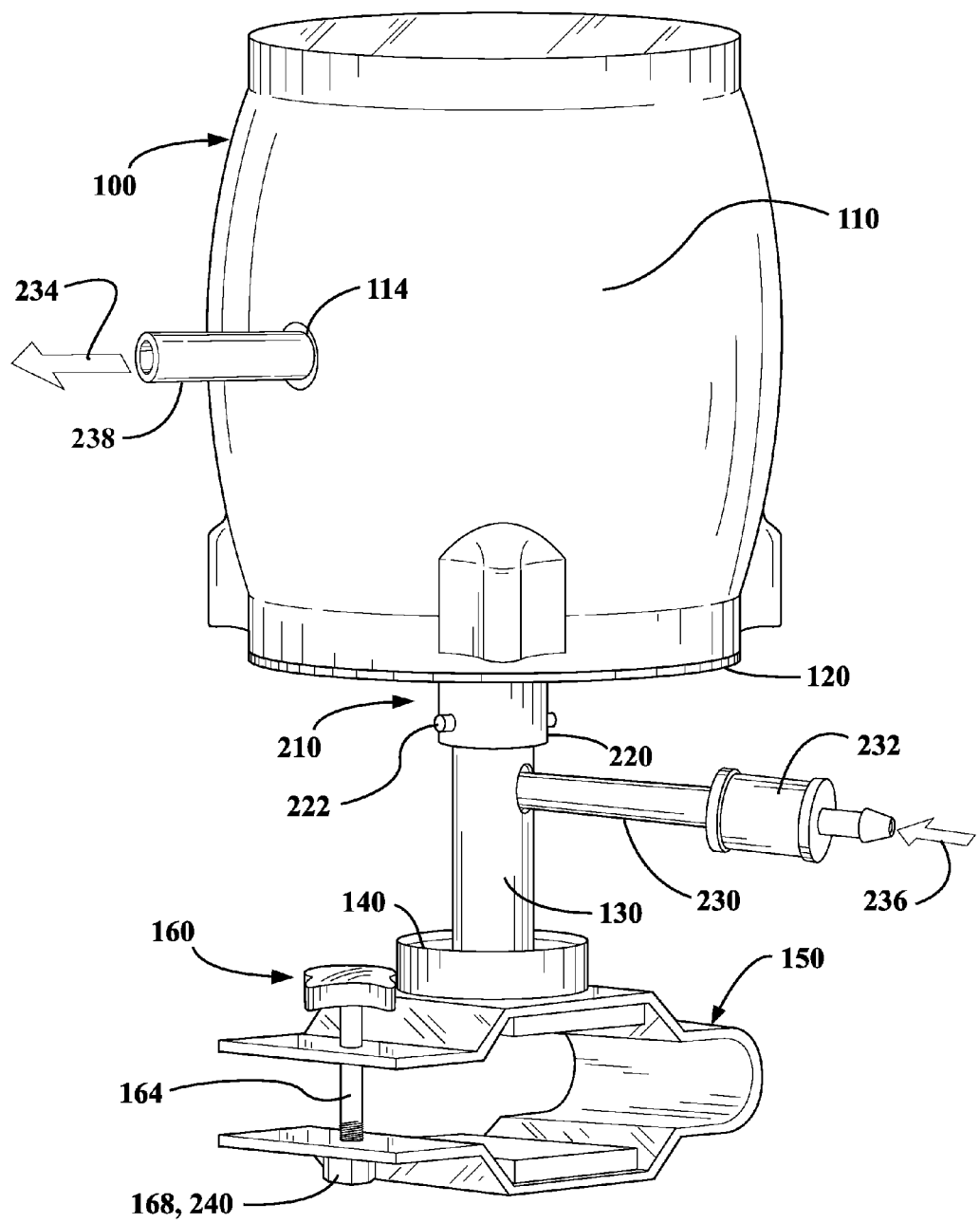
FIG. 2A illustrates a side perspective view of a gas supply system, in accordance with the first embodiment of the present invention.
Figure 2B:
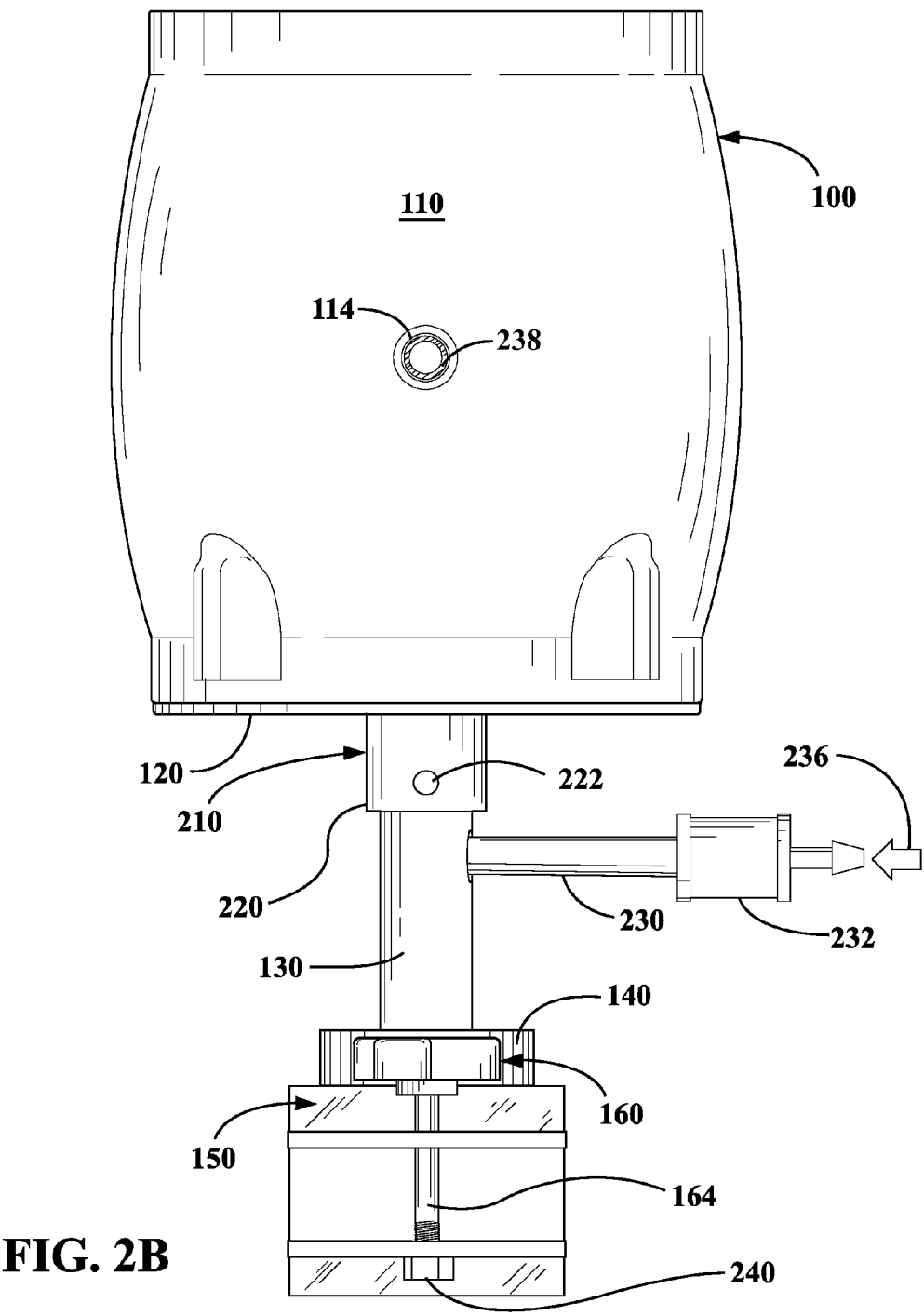
FIG. 2B illustrates a front perspective view of a gas supply system, in accordance with the first embodiment of the present invention.

FIG. 2A illustrates a side perspective view of the gas supply system 100, while FIG. 2B illustrates a front perspective view of the gas supply system 100. As previously discussed in conjunction with FIG. 1, the gas supply system 100 includes a housing 110, a main base 120, a rotating shaft 130, a rotational bearing 140, a base clamp 150 and an adjustable clamp screw 160. The gas supply system 100 additionally includes a main base connector assembly 210 with a main base sleeve 220 and a pin 222 securing the rotating shaft 130 to the main base sleeve 220. The sleeve 220 is disposed underneath the main base 120 on the rotating shaft 130 and includes a pair of corresponding apertures that also extend through the rotating shaft 130 for receiving the pin 222. As shown in FIG. 2A, inlet oxygen tubing 230 enters an aperture in the rotating shaft 130 (arrow 236 indicates the direction of oxygen flow) and travels generally axially to the interior of the housing 110 (see FIG. 4). Also, it can be seen in FIG. 2A that the oxygen tubing is provided with a check valve 232 having barbed end connectors 246 that regulates the flow of the gas through the tubing. A receiving nut 240 is disposed on the distal end 168 of the adjustable clamp screw 160 and assists in securing the adjustable clamp screw 160.

Figure 3:
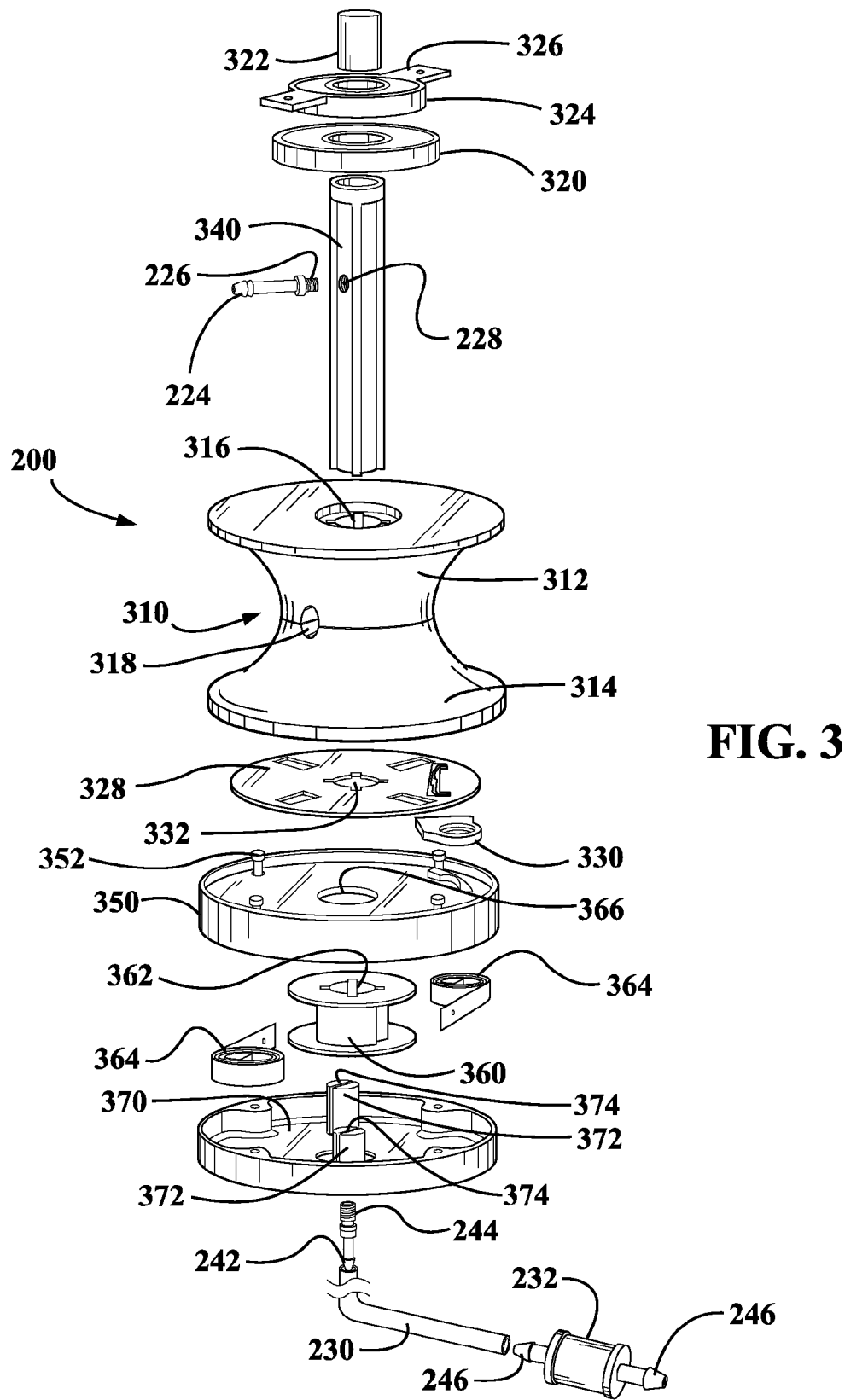
FIG. 3 illustrates an exploded view of the internal components of a gas supply system, in accordance with the first embodiment of the present invention.

FIG. 3 illustrates an exploded view of an internal component assembly 200 disposed inside the housing 110 of the gas supply system 100. The internal components illustrated in FIG. 3 include an oxygen tubing spool 310, a one-way bearing 320, a rotary damper 324, an interval locking device 328, 330, a universal shaft 322, a spring housing 350, 370, a spring torque spool 360, and a pair of spring grounding tabs 372. All of these components are contained in the housing 110. The spool 310 has a top portion 312 and a bottom portion 314 that receives and winds gas tubing, which is typically oxygen gas tubing, within the housing 110. The spool 310 receives the gas tubing from the aperture in the rotating shaft 130 described and illustrated in FIG. 2A. The one way bearing 320 is disposed above the spool 310 and has a universal shaft 322 rotationally connected thereto. The interval locking device 328, 330 locks the typically oxygen gas tubing in place at a plurality of locations or intervals along the typically oxygen gas tubing. The interval locking device 328, 330 comprises main base portion 328 and an interval locking triangle 330. The universal shaft 322 rotates together with the main keyed shaft 340 and is fixedly secured within the top bore 342 of the main keyed shaft 340 (see FIG. 4). The spring housing 350, 370 is disposed underneath the interval locking device 328, 330 and houses the two (2) constant force springs 364. The spring torque spool 360 secures the free ends of the springs 364 and rotates with the main keyed shaft 340, and is disposed at the bottom of the main keyed shaft 340. The pair of spring grounding tabs 372 receives the other ends of the springs 364 (in respective slots 374 of the spring grounding tabs 372), which ends are disposed opposite to the ends attached to the spring torque spool 360.

The rotary viscous damper 324 reduces the winding speed of the oxygen tubing so that the oxygen tubing does not wind too quickly as a result of the torque exerted thereon by the torsional springs 364. The one-way clutch bearing 320 is provided in conjunction with the rotary viscous damper 324 so that the rotation of the spool 310 with the oxygen tubing is only dampened in a single direction (i.e., only as the tubing is being wound around the spool 310 by the torque of springs 364). As a result of the one-way clutch bearing 320, the rotary viscous damper 324 only engages when the main keyed shaft 340 turns in the winding direction (i.e., when the oxygen tubing is being wound around the spool 310).

As shown in FIGS. 3 and 4, the main keyed shaft 340 passes through the keyed aperture 316 in the oxygen tubing spool 310, the keyed aperture 332 in the main base 328 of the interval locking device, the non-keyed apertures 366 in the top and bottom spring housing members 350, 370, and the keyed aperture 362 of the spring torque spool 360. The internal components having keyed apertures rotate with the main keyed shaft, while the internal components with non-keyed apertures do not rotate with the main keyed shaft 340. The top and bottom spring housing members 350, 370 are fastened together by means of spring housing screws 352 (e.g., four (4) spring housing screws—see FIG. 3).

As shown in FIGS. 3 and 4, the rotary damper 324 has opposed flanges 326. Each of these opposed flanges has a circular aperture disposed therethrough for accommodating a respective fastener 334. As shown in FIG. 4, these fasteners 334 secure the rotary damper 324 to the inside top surface of the housing 110.

Now, primarily with reference to FIGS. 3 and 4, the flow of the gas through the system 100 will be explained. Initially, the gas (e.g., oxygen) is conveyed through inlet oxygen tubing 230. After passing through the aperture in rotating shaft 130, oxygen tubing 230 connects to a lower end of barbed connector 242. As illustrated in FIG. 4, the barbed connector 242 is connected to an air tight connector 248, which prevents the gas (e.g., oxygen) from leaking out at the connection between the barbed connector 242 and the main keyed shaft 340. The annular projection of the air tight connector 248 may rotate relative to the annular groove disposed in barbed connector 242 so that the inlet oxygen tubing 230 may remain stationary during the rotation of the tubing spool 310. Then, the gas (e.g., oxygen) is conveyed axially through the hollow interior of the main keyed shaft 340 up to the generally horizontal barbed connector 224. As shown in FIGS. 3 and 4, the barbed connector 224 is provided with external threads 226 thereon that matingly engage with corresponding internal threads of the threaded aperture 228 in main keyed shaft 340. The barbed connector 224 is received within the tubing aperture 318 in oxygen tubing spool 310 (see FIGS. 3 and 4).

In one embodiment, the upper end portion of the barbed connector 242 may be provided with a plurality of external threads 244 for threadingly engaging with an internally threaded aperture disposed in a bottom end of the main keyed shaft 340.

FIGS. 5 and 6 illustrate a gas supply system 100', in accordance with a second embodiment of the present invention. In the second embodiment, the tubing spool 310 rotates about a horizontal axis, rather than a vertical axis.

Referring to FIGS. 5 and 6, it can be seen that, in many respects, the second exemplary embodiment is similar to that of the first embodiment. Moreover, many elements are common to both such embodiments. For the sake of brevity, the elements that the second embodiment of the gas supply system has in common with the first embodiment will not be discussed because these components have already been explained in detail above. Furthermore, in the interest of clarity, these elements are denoted using the same reference characters that were used in the first embodiment.

As shown in the sectional view of FIG. 6, the tubing spool 310, which includes a first side portion 313 and second side portion 315, rotates about a horizontal axis. The tubing spool 310 is structurally supported by a support yoke member 376. The support yoke member 376 comprises a base portion 380 and opposed upright side portions 378 extending upwardly from the base portion 380. The tubing spool 310 rotates relative to the stationary upright side portions 378 of the support yoke member 376. Turning again to FIG. 6, it can be seen that spring housing comprises a first side portion 351 and a second side portion 371. In one or more embodiments, the spring housing 351, 371 may be fixed relative to the support yoke member 376, while the spring torque spool 360 rotates with the tubing spool 310, relative to the stationary support yoke member 376.

The following is a list of reference characters that are utilized in the drawings of this application together with the components that they are used to represent (i.e., each component description is provided horizontally across from the corresponding component number):

100 Gas Supply System (Vertical Configuration)
100' Gas Supply System (Horizontal Configuration)
110 Housing
112 Cylindrical Shape of Housing
114 Aperture in Housing
120 Main Base
130 Rotating Shaft
132 Proximal End of Shaft
134 Distal End of Shaft
140 Rotational Bearing
150 Base Clamp
152 Corresponding Apertures in Base Clamp for Threaded Bolt
160 Adjustable Clamp Screw Assembly
162 Handle of Adjustable Clamp Screw
164 Threaded Bolt
166 Proximal End of Bolt
168 Distal End of Bolt
170 Clamp Surface for Accommodating Padding
172 Padding
200 Internal Component Assembly Inside Housing
210 Main Base Connector Assembly
220 Main Base Sleeve
222 Pin
224 Barbed Oxygen Tubing Connector
226 External Threads of Barbed Oxygen Tubing Connector
228 Threaded Aperture in Keyed Shaft
230 Incoming Oxygen Tubing
232 Oxygen Tubing Check Valve
234 Direction of Oxygen Flow (Outflow)
236 Direction of Oxygen Flow (Inflow)
238 Outgoing Oxygen Tubing
240 Receiving Nut
242 Barbed Oxygen Tubing Connector
244 External Threads of Barbed Oxygen Tubing Connector
246 Barbed End Connector of Oxygen Tubing Check Valve
248 Air Tight Connector
310 Oxygen Tubing Spool
312 Top Portion of Oxygen Tubing Spool
313 First Side Portion of Oxygen Tubing Spool
314 Bottom Portion of Oxygen Tubing Spool
315 Second Side Portion of Oxygen Tubing Spool
316 Keyed Aperture in Oxygen Tubing Spool
318 Tubing Aperture in Oxygen Tubing Spool
320 One-Way Bearing
322 Universal Shaft
324 Rotary Damper
326 Rotary Damper Flange
328 Main Base of Interval Locking Device
330 Interval Locking Triangle of Interval Locking Device
332 Keyed Aperture in Main Base of Interval Locking Device
334 Fastener for Rotary Damper
340 Main Keyed Shaft
342 Top Bore of Main Keyed Shaft
350 Top Spring Housing
351 First Side Portion of Spring Housing
352 Spring Housing Screws
360 Spring Torque Spool
362 Keyed Aperture of Spring Torque Spool
364 Constant Force Spring
366 Non-Keyed Aperture in Spring Housing
370 Bottom Spring Housing
371 Second Side Portion of Spring Housing
372 Spring Grounding Tabs
374 Slots in Spring Grounding Tabs
376 Support Yoke Member
378 Upright Side Portion of Support Yoke Member
380 Base Portion of Support Yoke Member The present invention provides a gas supply system. The gas supply system is adapted to be used for delivery of a gas from a gas supply, for example, an air supply cylinder, to a nasal cannula. The gas supply system enables the patient to move conveniently and freely from one place to another inside a room while being administered a gas from the disclosed gas supply system. Moreover, the gas supply system prevents the tube from lying on a floor of the room and being dragged thereof along the floor.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A gas supply system, comprising:
a housing that includes an aperture, a spool, a one way bearing circumscribing a vertically-oriented small shaft, an interval locking device, a vertically-oriented keyed shaft, a spring housing, and a spring torque spool configured to secure a free end of a spring;
a main base that stabilizes said housing in an upright perpendicular position;
a vertically-oriented rotating shaft that has a proximal end and a distal end where said main base is disposed on said distal end of said vertically-oriented rotating shaft;
a base clamp having opposed upper and lower offset portions, said upper offset portion having a top surface, said base clamp further including a pair of corresponding apertures, said base clamp configured to secure said gas supply system to a tubular shaped object;
a rotational bearing that is disposed on said top surface of said base clamp and at said proximal end of said vertically-oriented rotating shaft, said rotational bearing connecting the vertically-oriented rotating shaft to said base clamp; and an adjustable clamp screw that has a handle and a threaded bolt with a proximal end and a distal end wherein said proximal end of said threaded bolt is attached to and perpendicularly extends from said handle of said adjustable clamp screw.

2. The system according to claim 1, wherein said housing is generally cylindrical in shape.

3. The system according to claim 1, wherein said base clamp is configured to support padding disposed thereon, said padding configured to prevent damage to said base clamp or said tubular shaped object.

4. The system according to claim 1, wherein said adjustable clamp screw is rotated and screwed through said pair of corresponding apertures of said base clamp to tighten said base clamp around said tubular shaped object.

5. The system according to claim 1, wherein said spool has a top inverted frusto-conical portion and a bottom frusto-conical portion, said top inverted frusto-conical portion being disposed at a higher elevation than said bottom frusto-conical portion relative to a horizontal reference plane beneath said gas supply system, said spool being configured to receive and wind oxygen gas tubing within said housing from said aperture.

6. The system according to claim 5, wherein said interval locking device is disposed between an upper portion of said spring housing and said one way bearing, said interval locking device configured to lock said oxygen gas tubing at a plurality of locations or intervals along the rotation of said spool.

7. The system according to claim 5, wherein said spring housing is placed on said vertically-oriented keyed shaft underneath said interval locking device such that said spring housing is disposed at a lower elevation than said interval locking device relative to a horizontal reference plane beneath said gas supply system, said spring housing configured to house said spring.

8. The system according to claim 1, wherein said vertically-oriented keyed shaft includes one or more elongated protruding portions extending radially outward from a circumferential surface thereof.

9. The system according to claim 1, wherein said spring torque spool rotates with said keyed shaft and is disposed at a bottom of said vertically-oriented keyed shaft.

10. The system according to claim 1, wherein said gas supply system includes a sleeve disposed underneath said main base such that said sleeve is disposed at a lower elevation than said main base relative to a horizontal reference plane beneath said gas supply system, said sleeve being attached to said distal end of said vertically-oriented rotating shaft by a pin.

11. The system according to claim 1, wherein said gas supply system includes a receiving nut at said distal end of said threaded bolt.

* * * * *